(12) United States Patent
Smith et al.

(10) Patent No.: US 9,320,854 B2
(45) Date of Patent: Apr. 26, 2016

(54) DOSE SETTING MECHANISM WITH MAXIMUM DOSE LIMITED ELEMENT

(75) Inventors: Christopher James Smith, Holmes Chapel (GB); Philip Oakland, Stockport (GB)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 487 days.

(21) Appl. No.: 13/516,255

(22) PCT Filed: Dec. 16, 2010
(Under 37 CFR 1.47)

(86) PCT No.: PCT/EP2010/069863
§ 371 (c)(1),
(2), (4) Date: Jan. 26, 2013

(87) PCT Pub. No.: WO2011/073302
PCT Pub. Date: Jun. 23, 2011

(65) Prior Publication Data
US 2013/0218096 A1 Aug. 22, 2013

(30) Foreign Application Priority Data

Dec. 18, 2009 (EP) .................................. 09179998

(51) Int. Cl.
*A61M 5/315* (2006.01)
*A61M 5/168* (2006.01)

(52) U.S. Cl.
CPC ........... *A61M 5/31535* (2013.01); *A61M 5/168* (2013.01); *A61M 5/31551* (2013.01); *A61M 5/31561* (2013.01); *A61M 5/31525* (2013.01); *A61M 2005/3154* (2013.01)

(58) Field of Classification Search
CPC .......... A61M 5/3155; A61M 5/31551; A61M 5/31525; A61M 2005/3154; A61M 5/31591; A61M 5/3153; A61M 5/31535; A61M 5/31536; A61M 5/31538; A61M 5/31548; A61M 5/31528; A61M 5/31533; A61M 5/31553; A61M 5/31563; A61M 5/168; A61M 5/31561
USPC .......... 604/208, 207, 210, 209, 211, 212, 246
See application file for complete search history.

(56) References Cited

U.S. PATENT DOCUMENTS

| 5,514,097 A | 5/1996 | Knauer |
| 2008/0154211 A1* | 6/2008 | Moller ........................... 604/211 |
| 2011/0034902 A1* | 2/2011 | Markussen ................... 604/506 |

FOREIGN PATENT DOCUMENTS

| EP | 1074273 A1 | 2/2001 |
| EP | 1559443 A1 | 8/2005 |

(Continued)

OTHER PUBLICATIONS

Form PCT/IPEA/416, Notification of Transmittal of the International Preliminary Report on Patentability.

(Continued)

*Primary Examiner* — Kami A Bosworth
*Assistant Examiner* — Hamza Darb
(74) *Attorney, Agent, or Firm* — McDonnell Boehnen Hulbert & Berghoff LLP

(57) ABSTRACT

A dose setting mechanism for a drug delivery device is provided comprising first maximum dose stop features (1) on a first component part (2) of the drug delivery device and corresponding second maximum dose stop features (3) on a second component part (4) of the drug delivery device, with the first and second maximum dose stop features (1, 3) being designed to limit a relative movement between the first and second component parts (2, 4). To limit the maximum dose which can be chosen, a maximum dose limiting device (5, 10, 10', 10'', 10''') is provided interposed on the first component part (2) between the first and second maximum dose stop features (1, 3).

7 Claims, 3 Drawing Sheets

(56) References Cited

FOREIGN PATENT DOCUMENTS

| | | |
|---|---|---|
| EP | 1603611 B1 | 12/2005 |
| EP | 1776975 A2 | 4/2007 |
| GB | 1388828 | 3/1975 |
| JP | 2008531150 A | 8/2008 |
| WO | 0154757 A1 | 8/2001 |
| WO | 0171293 A1 | 9/2001 |
| WO | 2006089767 A1 | 8/2006 |

OTHER PUBLICATIONS

English Translation of Notice of Reasons for Rejection issued in Japanese Patent Application No. 2012-543740 dated Sep. 9, 2014.

* cited by examiner

DOSE SETTING MECHANISM WITH MAXIMUM DOSE LIMITED ELEMENT

CROSS REFERENCE TO RELATED APPLICATIONS

The present application is a 35 U.S.C. 371 National Application of PCT/EP2010/069863 filed Dec. 16, 2010, which claims priority to European Patent Application No. 09179998.1 filed Dec. 18, 2009, the entire contents of which are incorporated entirely herein by reference.

The present invention concerns a dose setting mechanism for drug delivery devices.

In the manufacture of medicinal devices there are often advantages in producing a family of products based on a common device platform. For example, simplification of manufacturing processes or reductions in cost of goods are such advantages.

A common means of dispensing an injectable medicinal product is a drug delivery device having a variable dose injection means. When such a drug delivery device platform is to be used for a number of injectable medicinal products, the designed maximum dose of the platform device may not be appropriate for each of the drugs to be delivered. One example may be long acting insulin and short acting insulin, which is described below.

In the state of the art means for limiting the maximum dose of a drug delivery device are known. U.S. Pat. No. 5,514,097 discloses a self administered injection pen apparatus, wherein a dose-limiting sleeve is coupled to a dose knob stop assembly consisting of two distinct structures. In one embodiment, the dose limiting sleeve is a tubular structure having open ends on both sides. One of the two distinct structures is positioned within the one open end. This structure includes a set of grooves and the dose limiting sleeve tubular structure includes a set of rails. The sets of grooves and rails rotationally couple the one of the two structures and the dose limiting sleeve tubular structure so that the one of the two structures and the dose limiting sleeve tubular structure rotate together. The dose limiting sleeve according to U.S. Pat. No. 5,514,097 can be selectively engaged by the user (i.e. a healthcare professional as well as a patient) applying a special tool to adjust the relative position of this sleeve so as to set the predetermined and pre-set limit.

The principal assembly of a drug delivery device and its drive mechanism are disclosed in the patent EP 1 603 611 B1 of the present applicant, to which reference is made for further details.

Drug delivery devices of the generic kind are applied where regular injection by persons without formal medical training, i.e. patients, occurs. However, these circumstances require some provisions for such drug delivery devices. The devices must be robust in construction, easy to use both in terms of the manipulation of the parts and understanding by a patient of its operation. In the case of those patients with for instance diabetes, many users will be physically infirm and may also have impaired vision.

Therefore, one significant drawback of the limiting means in the state of the art is the possibility that the patient himself can alter the maximum dose without supervision of a healthcare professional. This may lead to an overdose of the drug to be delivered due to faulty operation.

Another drawback can be identified in the complex technique of the limiting means in the state of the art. As becomes apparent from column 20, lines 30 to 32, of U.S. Pat. No. 5,514,097, two distinct structures are used together with a dose limiting sleeve and a number of grooves and rails to obtain a variable length, i.e. to vary the maximum dose dispensed from the respective device. Such a construction does not contribute to a simplification of manufacturing processes or reductions in cost of goods.

It is an object of the present invention to provide an improved dose setting mechanism allowing for the maximum dose of an drug delivery device (injection device) to be modified.

The above-mentioned drawbacks have been overcome by the present invention, which is a simple means for limiting in advance the maximum dose that a user can set with a drug delivery device having variable dose function. In other words, according to the present invention a device is provided allowing for the maximum dose of a drug delivery device to be modified with the optional addition of only one single component which is the maximum dose limiting device. Furthermore, this one single change component, i.e. a dose setting mechanism having a maximum dose limiting sleeve, is an extremely simple component, which does not require any special surface finishing, such as printing or the like, and which does not require complicated or precise assembly.

In particular, a dose setting mechanism for a drug delivery device is provided, comprising first maximum dose stop features on a first component part of the drug delivery device and corresponding second maximum dose stop features on a second component part of the drug delivery device, with the first and second maximum dose stop features being designed to limit a relative movement between the first and second component parts. Further, a maximum dose limiting device is provided interposed on the first component part between the first and second maximum dose stop features and having mating features on a first end fitting to the first maximum dose stop features and replica stop features on a second end replicating the first maximum dose stop features.

Preferably, the maximum dose limiting device is a maximum dose limiting sleeve, comprising a tubular body with an essentially cylindrical cross-section having open ends on opposite sides in the tubular axis, with the mating features being provided on the one open end of the body fitting to the first maximum dose stop features of the drug delivery device, and with the replica stop features being provided on the other open end of the body replicating the first maximum dose stop features of the drug delivery device. Therein, the mating features define a position of the maximum dose limiting sleeve both in rotation and translation directions with respect to the drug delivery device, wherein the maximum dose limiting sleeve is designed with an interference fit to the diameter of the first component part of the drug delivery device.

The inner diameter of the maximum dose limiting sleeve may be designed with an interference fit to the outer diameter of the first component part of the drug delivery device. Moreover, the outer diameter of the maximum dose limiting sleeve may be the same as the outer diameter of the first maximum dose stop features of the drug delivery device. Alternatively, the outer diameter of the maximum dose limiting sleeve may be less as the outer diameter of the first maximum dose stop features of the drug delivery device, preferably between 80% to 99% of the outer diameter of the first maximum dose stop features of the drug delivery device, particularly preferably between 90% and 95% of the outer diameter of the first maximum dose stop features of the drug delivery device.

Preferably, the length of the maximum dose limiting sleeve and/or the angular location of said replica stop features with respect to the second maximum dose stop features of the maximum dose limiting sleeve are designed according to a predefined, desired limited dose value. More preferably, the maximum dose stopping torque is transmitted through the maximum dose limiting sleeve directly to the first maximum dose stop features of the drug delivery device.

In addition to the above, a drug delivery device is provided, which comprises a housing, a dose setting mechanism as described above, a drive mechanism including a spindle and interacting with said dose setting mechanism at least during setting of a dose, and a cartridge filled with a drug and attachable to said housing and/or said drive mechanism.

In contrast to the state of the art, where the maximum dose stop can be altered by either the user/patient or a healthcare professional, the maximum dose is factory-preset by inserting the maximum dose limiting sleeve of the present invention while assembling the drug delivery device, so that no manipulation of the maximum dose can be done.

The present invention further refers to a drug delivery device comprising a dose setting mechanism, the dose setting mechanism comprising
   first maximum dose stop features on a first component part of said drug delivery device,
   corresponding second maximum dose stop features on a second component part of said drug delivery device, with the first and second maximum dose stop features being designed to limit a relative rotational movement between said first and second component parts,
   a maximum dose limiting device interposed on said first component part between said first and second maximum dose stop features and having mating features on a first end fitting to said first maximum dose stop features and replica stop features on a second end replicating said first maximum dose stop features.

In this drug delivery device said maximum dose limiting device preferably is a maximum dose limiting sleeve, comprising
   a tubular body with an essentially cylindrical cross-section having open ends on opposite sides in the tubular axis,
   with said mating features being provided on the one open end of said body fitting to said first maximum dose stop features of said drug delivery device, and
   with said replica stop features being provided on the other open end of said body replicating said first maximum dose stop features of said drug delivery device,
   said mating features defining a position of said maximum dose limiting sleeve both in rotation and translation directions with respect to said drug delivery device,
   said maximum dose limiting sleeve being designed with an interference fit to the diameter of said first component part of said drug delivery device.

In this drug delivery device the inner diameter of said maximum dose limiting sleeve may be designed with an interference fit to the outer diameter of the first component part of said drug delivery device.

The outer diameter of said maximum dose limiting sleeve may be the same as the outer diameter of said first maximum dose stop features of said drug delivery device.

The length of said maximum dose limiting sleeve and/or the angular location of said replica stop features with respect to said second maximum dose stop features of said maximum dose limiting sleeve may be designed according to a pre-defined, desired limited dose value.

When the replica stop features are in contact with the second component part, a maximum dose stopping torque is preferably transmitted through said maximum dose limiting sleeve directly to said first maximum dose stop features of said drug delivery device.

The drug delivery device according to the present invention preferably further comprises a housing, a drive mechanism including a spindle and interacting with said dose setting mechanism at least during setting of a dose, and a cartridge filled with a drug and attachable to said housing and/or said drive mechanism.

The term "drug", as used herein, preferably means a pharmaceutical formulation containing at least one pharmaceutically active compound,
   wherein in one embodiment the pharmaceutically active compound has a molecular weight up to 1500 Da and/or is a peptide, a proteine, a polysaccharide, a vaccine, a DNA, a RNA, a antibody, an enzyme, an antibody, a hormone or an oligonucleotide, or a mixture of the above-mentioned pharmaceutically active compound,
   wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis,
   wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(02)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

In the following, the invention will be described by way of examples and referring to the Figures.

FIG. 2 shows a schematic view the of the drug delivery device of

Figure 1:
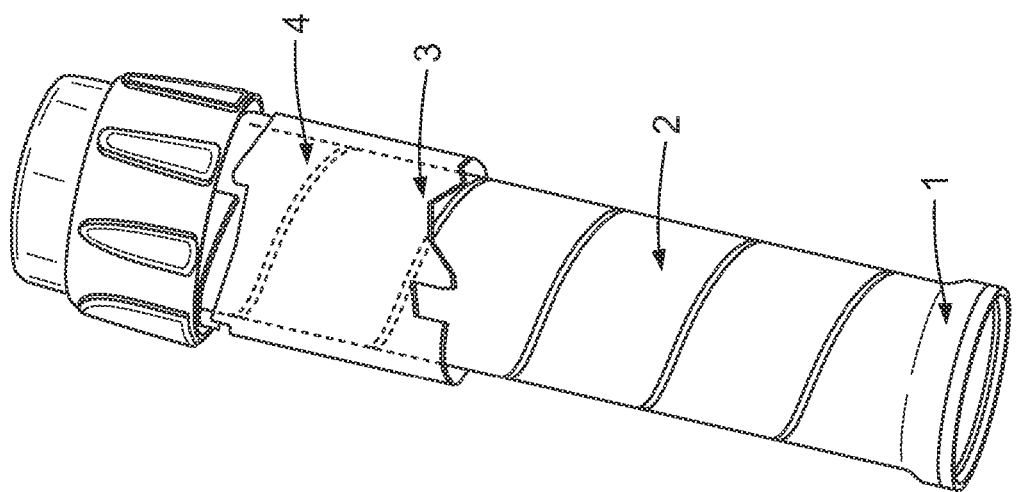
FIG. 1 shows a schematic view of a drug delivery device.
Figure 4:
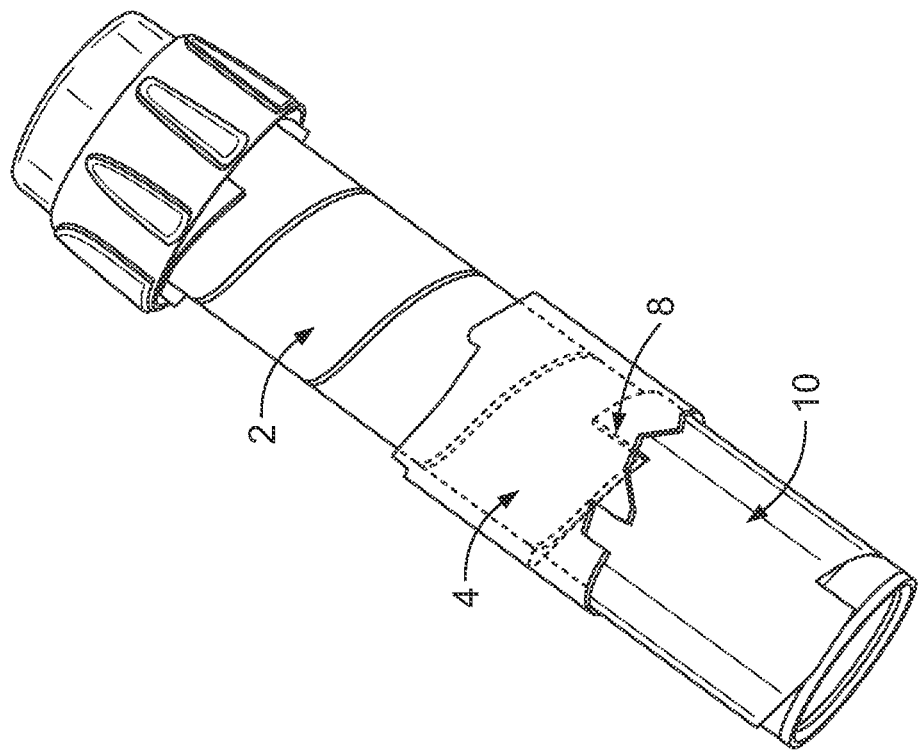
Figure 3:
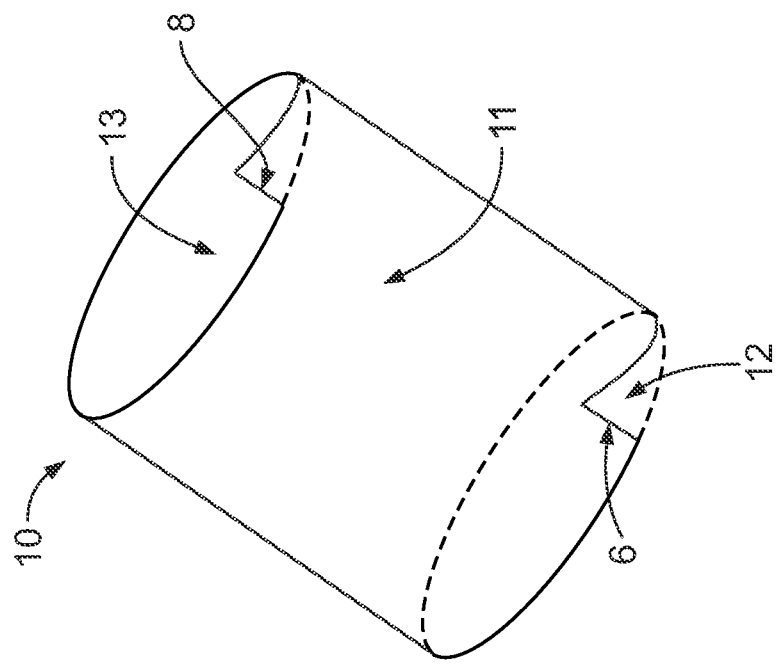
Figure 5:
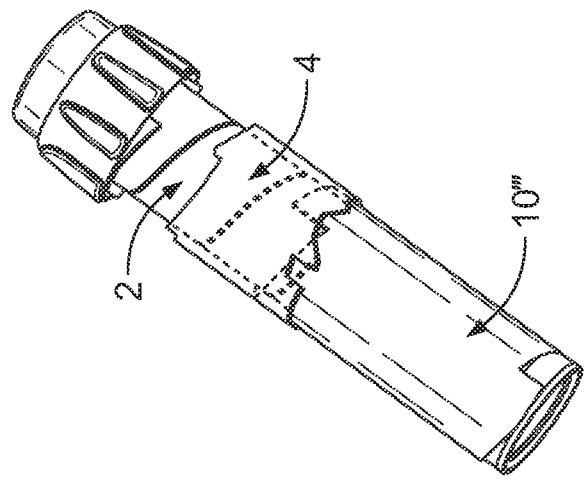
Figure 5:
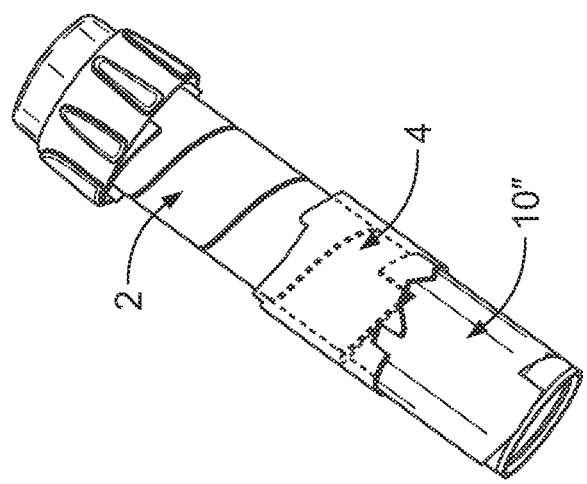
Figure 5:
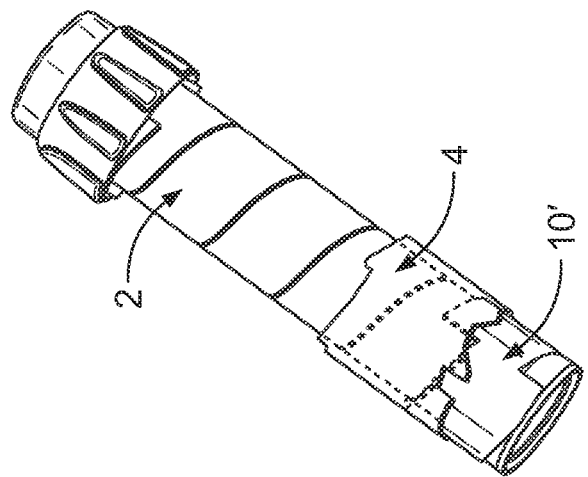

FIG. 1 having applied the maximum dose limiting device,

FIG. 3 shows a schematic drawing of a maximum dose limiting sleeve,

FIG. 4 shows schematically the mating of the maximum dose limiting sleeve and the second component part, FIG. 5 shows schematic views applying maximum dose limiting sleeves with different lengths.

Hereinafter, the features of the present invention are described with reference to the drug delivery device disclosed in EP 1 603 611 B1 of the present applicant.

Although the present invention is described with reference to this specific drug delivery device, the dose setting mechanism may be applicable to other variable dose injection devices, where the maximum dose is limited in a similar manner. In other words, it may equally be applied to any drug delivery device where the maximum dose stop is determined by features of two separate components moving towards one another and making contact when the maximum dose is reached. This could apply both to rotationally moving components, e.g. in a dialable variable dose pen, or axially travelling components, e.g. in a pull-push fixed dose pen. Furthermore, the present invention is described with respect to disposable drug delivery devices, but is applicable also for reusable drug delivery devices.

In the drug delivery device disclosed in EP 1 603 611 B1, the maximum dose stop (also known as the 80 unit stop) is achieved by contact between protrusions 1 (i.e. maximum dose stop feature) moulded on the outer surface of a dose dial sleeve 2 (correlating to the first component part) and corresponding protrusions 3 (i.e. maximum dose stop feature) moulded on the inner surface of a component part 4 (e.g.

thread insert). This is shown in FIG. 1. Corresponding protrusions (i.e. maximum dose stop features) are also present on the opposite sides of the first and second component parts 2, 4.

The dose setting mechanism according to the present invention comprises an additional component 5 that may optionally be included in the assembly of the drug delivery device of the generic kind. As can be taken from FIG. 2 this additional component is designed as a sleeve 10 having a tubular body 11 with an essentially cylindrical cross-section having open ends 12, 13 on opposite sides in the tubular axis. The dose setting mechanism 5 is assembled over the first component part 2 of the drug delivery device, for instance an injection pen. The dose setting mechanism has mating features 6, which fit to the first maximum dose stop features 1 of the first component part 2, and replica stop features 8, which replicate the stop features of the first component part 2.

Figure 2:
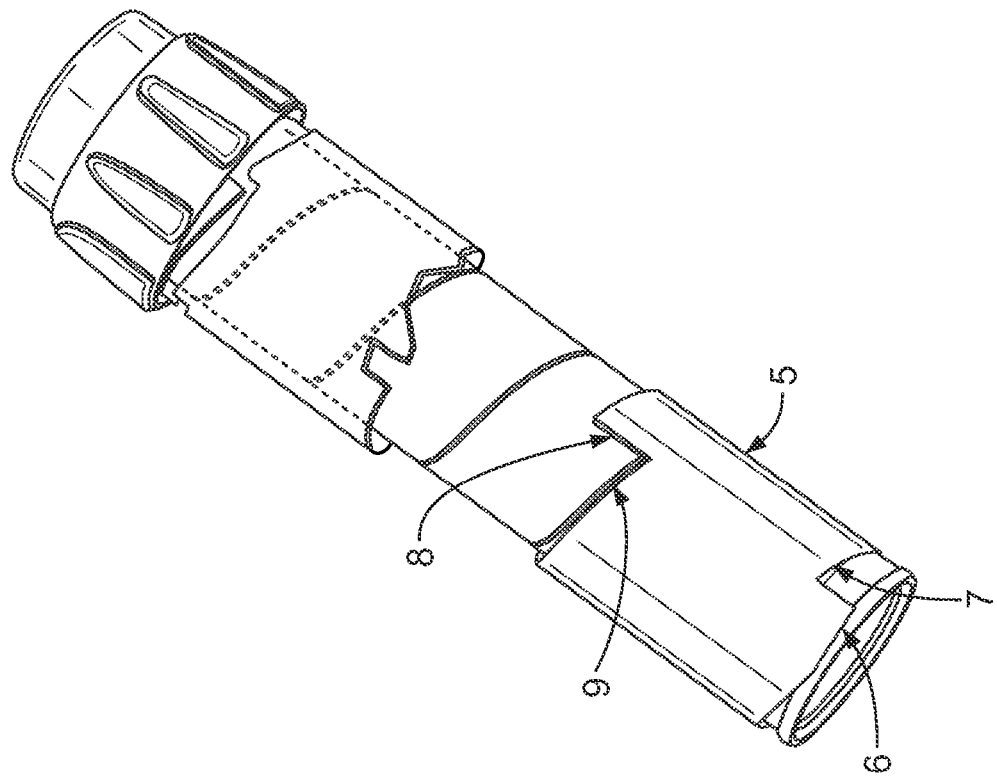

The mating features 6, combined with an interference fit to the diameter of the first component part 2, locate component 5 in both rotational direction and translational (axial) direction to first component part 2. The other end of component 5 carries the replica stop features 8. An illustrative example of component is shown in FIG. 2.

In this particular embodiment, component 5 is a maximum dose limiting sleeve 10, as shown in FIG. 3. The inner diameter of the maximum dose limiting sleeve 10 is designed with an interference fit to the first component part 2 to hold it in position. However, the interference fit does not have to provide the maximum dose stopping torque. When the modified maximum dose has been dialled and the replica stop features 8 are in contact with the second component part, the stopping torque is transmitted through the maximum dose limiting sleeve 10 directly to the mating features 6 of the first component part 2.

The outer diameter of the maximum dose limiting sleeve 10 is the same as the diameter of first maximum dose stop features 1 of the first component part 2. In other words, the thickness of the maximum dose limiting sleeve 10 is the same as the height of the maximum dose stop protrusions moulded to the first component part 2. The non-stop feature portion of the end surfaces follow the same helix as the thread of the first component part 2 so that they do not interfere with the thread of the first component part 2. Therefore, the maximum dose limiting sleeve 10 does not interfere with the travel of any of further mechanism components, in particular the rotation of the first component part 2 within the second component part 4. Hence, the normal operation of the drug delivery device (up to the modified maximum dose) is not affected by the presence of the maximum dose limiting sleeve 10. The positions of the second component part 4, the maximum dose limiting device 5 and first component part 2, when the modified maximum dose has been dialled, are shown in FIG. 4.

By suitably designing the length of the maximum dose limiting sleeve 10 and the angular location of the replica stop features 8 relative to the first maximum dose stop features 1 of the first component part 2, the maximum dose can be reduced to any desired value. This is illustrated in FIG. 5. In this example, three maximum dose limiting sleeves 10', 10", 10''' each differ in length by one thread pitch of the first component part 2. Therefore, each increment of the maximum dose limiting sleeve 10 reduces the maximum dose that can be dialled by one revolution of the first component part 2. In the case of the drug delivery device disclosed in EP 1 603 611 B1, this reduces the maximum dose in steps of 20 units.

The dose setting mechanism according to the present invention allows for the maximum dose of a drug delivery device to be modified with the optional addition of only one single change component. Furthermore, this change component, i.e. the maximum dose limiting sleeve 10, is an extremely simple component, which does not require printing and which does not require complicated or precise assembly.

As an alternative solution to the dose setting mechanism disclosed herein, modifications of existing components are imaginable. For instance, these could be modifications to the components defining the maximum dose stop, i.e. the first component part 2 or the second component part 4. The first component part 2 (e.g. a dose dial sleeve) in the drug delivery device disclosed in EP 1 603 611 B1 is a particularly challenging component to manufacture and also requires a printing step. The second component part 4 (e.g. a thread insert) in the drug delivery device disclosed in EP 1 603 611 B1 is also reasonably complex to manufacture (compared to the dose setting mechanism) and requires a highly polished "lens" surface to form the dose viewing window.

Moreover, the second component part 4 and in particular the first component part 2 are also critical to performance and any variation in these components between device variants and could potentially affect the performance of these device variants.

One main advantage of the present invention is therefore in keeping the cost of goods for the device variants to a minimum. A further advantage of the dose setting mechanism is that performance of the basic mechanism is not affected.

EXAMPLES

The dose setting mechanism can be used whenever there is a "family" of devices, where different drugs or drug concentrations are delivered by devices that are based around a common platform of a drug delivery device.

Example 1

Long Acting Insulin and Short Acting Insulin (e.g. "Lantus" and "Apidra")

For reasons of safety of the patient, it might be preferred to reduce the maximum possible dose of the short acting insulin in a delivery device compared to the maximum dose of the long acting insulin. Therefore, the present invention is useful in providing both types of insulin with different maximum doses based on one single drug delivery device, for instance the drug delivery device disclosed in EP 1 603 611 B1 having different dose setting mechanisms.

Example 2

Insulin Glargine (Lantus)/AVE-0010 Combination Delivery Devices

In one concept for the delivery of this combination drug, the two active ingredients are provided together in a single formulation and a single cartridge. Patients need to deliver a variable dose of Lantus and will therefore receive a variable dose of AVE-0010 (glucagon-like peptide 1 (GLP-1) receptor agonist and an insulin secretagogue). In order to ensure that all patients receive an efficacious dose of AVE-0010, irrespective of Lantus dose, it is likely that several formulations will be required, e.g. each formulation has a fixed (U100) concentration of Lantus but a variable concentration of AVE-0010. Depending on the Lantus dose required a patient would be prescribed the particular formulation that will best give them their correct AVE-0010 dose. These formulations would each be delivered in a separate delivery device, but this would ideally be based around the same device platform. In order to ensure that a patient receiving an unsuitable formulation does not receive an overdose of AVE-0010 it would be an advantage to reduce the maximum does that the device could deliver.

The invention claimed is:

1. A drug delivery device comprising a dose setting mechanism, the dose setting mechanism comprising
    first maximum dose stop features on a first component part of said drug delivery device, wherein the first maximum dose stop features comprise protrusions moulded onto an outer surface of the first component part,
    corresponding second maximum dose stop features on a second component part of said drug delivery device,
    with the first and second maximum dose stop features being designed to limit a relative rotational movement between said first and second component parts,
    a maximum dose limiting device comprising a maximum dose limiting sleeve,
    the maximum dose limiting sleeve interposed on said first component part between said first and second maximum dose stop features and
    having mating features on a first end fitting to said first maximum dose stop features and
    replica stop features on a second end replicating said first maximum dose stop features, wherein a thickness of the maximum dose limiting sleeve is the same as a height of the protrusions moulded on to an outer surface of the first component part.

2. The drug delivery device of claim 1, wherein the maximum dose limiting sleeve comprises
    a tubular body with an essentially cylindrical cross-section having open ends on opposite sides in the tubular axis,
    with said mating features being provided on the one open end of said body fitting to said first maximum dose stop features of said drug delivery device, and
    with said replica stop features being provided on the other open end of said body replicating said first maximum dose stop features of said drug delivery device,
    said mating features defining a position of said maximum dose limiting sleeve both in rotation and translation directions with respect to said drug delivery device,
    said maximum dose limiting sleeve being designed with an interference fit to the diameter of said first component part of said drug delivery device.

3. The drug delivery device according to claim 2, wherein an inner diameter of said maximum dose limiting sleeve is designed with an interference fit to an outer diameter of the first component part of said drug delivery device.

4. The drug delivery device according to claim 2, wherein an outer diameter of said maximum dose limiting sleeve is the same as an outer diameter of said first maximum dose stop features of said drug delivery device.

5. The drug delivery device according to claim 2, wherein a length of said maximum dose limiting sleeve and/or an angular location of said replica stop features with respect to said second maximum dose stop features of said maximum dose limiting sleeve are designed according to a predefined, desired limited dose value.

6. The drug delivery device according to claim 2, wherein, when the replica stop features are in contact with the second component part, a maximum dose stopping torque is transmitted through said maximum dose limiting sleeve directly to said first maximum dose stop features of said drug delivery device.

7. The drug delivery device according to claim 1, further comprising a housing, a drive mechanism including a spindle and interacting with said dose setting mechanism at least during setting of a dose, and a cartridge filled with a drug and attachable to said housing and/or said drive mechanism.

* * * * *